US00PP26760P3

(12) United States Plant Patent
Hansoti

(10) Patent No.: US PP26,760 P3
(45) Date of Patent: May 24, 2016

(54) ***ZAMIOCULCAS* PLANT NAMED 'HANSOTI13'**

(50) Latin Name: *Zamioculcas zamiifolia*
Varietal Denomination: HANSOTI13

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 228 days.

(21) Appl. No.: 13/998,813

(22) Filed: Dec. 9, 2013

(65) Prior Publication Data

US 2015/0163985 P1 Jun. 11, 2015

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Zamioculcas* cultivar named 'HANSOTI13' is disclosed, characterized by unique compact growth, an urn shaped plant shape and glossy, dark green leaves. The new variety is a *Zamioculcas*, typically produced as an indoor ornamental plant.

3 Drawing Sheets

Figure 1:
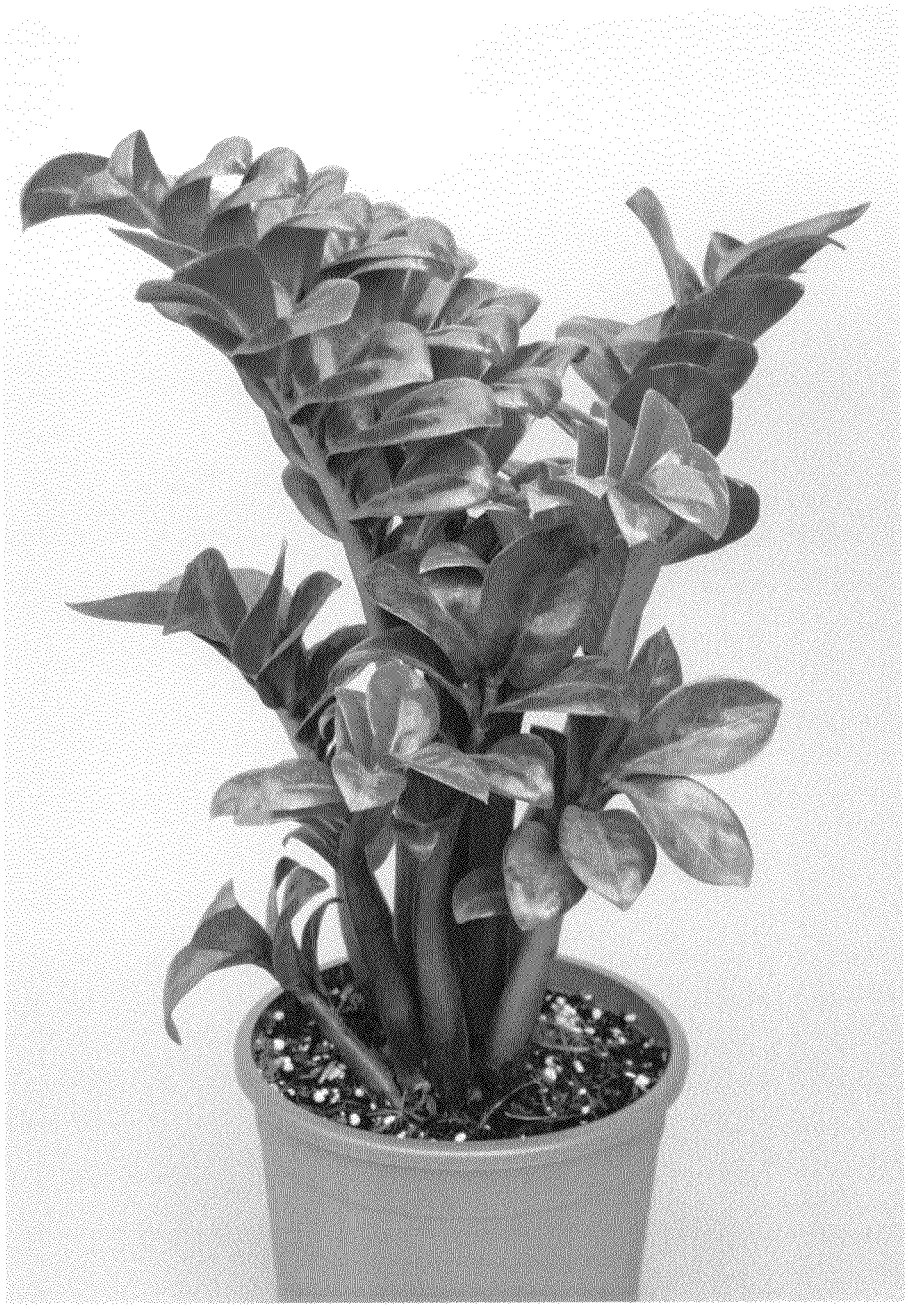

Latin name of the genus and species: *Zamioculcas zamiifolia.*

Variety denomination: 'HANSOTI13'.

BACKGROUND OF THE INVENTION

The present invention relates to a new and distinct cultivar of *Zamioculcas*, botanically known as *Zamioculcas zamiifolia*, and hereinafter referred to by the name 'HANSOTI13'. The new *Zamioculcas* is a naturally-occurring branch mutation from an unnamed, unpatented variegated selection of *Zamioculcas zamiifolia*. The new *Zamioculcas* was discovered and selected by the inventor, Ashish Hansoti as a single, green compact leaf from this variegated plant grown in a simple plastic greenhouse at Vangani, near Mumbai in India in the year 2009.

Asexual reproduction of the single leaf by vegetative cuttings at Vangani, near Mumbai in India showed variable characteristics. Further repeated selection for specific characteristics displayed by 'HANSOTI13', especially short internode space, resulted in the new *Zamioculcas* which is stable and reproduces true to type in successive generations.

SUMMARY OF THE INVENTION

The cultivar 'HANSOTI13' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HANSOTI13'. These characteristics in combination distinguish 'HANSOTI13' as a new and distinct *Zamioculcas* cultivar:

1. Very short internode spaces giving compact growth and more numerous leaflets per leaf.

2. Stiff, strong and upright leaves with characteristic curvature of petiole and rachis resulting in overall urn shaped plant.
3. Shiny dark green-colored leaves.

PARENT COMPARISON

Plants of the new cultivar 'HANSOTI13' are similar to the parent, an unpatented, unnamed, *Zamioculcas zamiifolia* in most horticultural characteristics. However the new variety, 'HANSOTI13' differs from the parent in the following characteristics:

1. Much more compact growing that parent variety.
2. Space between leaflets much reduced.
3. Leaves smaller and thicker. Darker green under same cultural conditions.
4. Leaves more upright (or vertical) with typical S shaped curve of rachis.
5. Growth rate is as fast or faster than the parent variety.

COMMERCIAL COMPARISON

'HANSOTI13' is best compared with the unpatented commercial variety *Zamioculcas zamiifolia*, the new variety, 'HANSOTI13' differs in the following characteristics:

1. Plants of the new variety have leaflets with a very short internode space between leaflets and so many more leaflets per leaf than the typical commercial *Zamioculcas zamiifolia* leaf of similar length.
2. Plants of the new variety display an overall compactness and are short in stature even though eventually they can grow to 50 cm or more.

'HANSOTI13' can also be compared to the commercial variety *Zamioculcas zamiifolia* 'Zamicro' U.S. Plant Pat. No. 19,314. 'HANSOTI13' differs in the following characteristics:

1. Plants of the new *Zamioculcas* have a very short internode space between leaflets and so are more compact and shorter than plants of the cultivar 'Zamicro', with more leaflets per leaf of similar length. Per 20 cm of leaf, the new variety has 1.5 to 2 times more leaflets.

2. Plants of the new variety produce larger leaflets, averaging 6.0 cm in length, compared to 4.6 in length for this comparator. Average leaflet width of the new variety is 3.0 cm compared to 1.7 cm leaflet width of 'Zamicro'.

BRIEF DESCRIPTION OF THE PHOTOGRAPHS

The accompanying colored photographs illustrate the overall appearance of the new *Zamioculcas* showing the colors as true as it is reasonably possible to obtain in colored reproductions of this type. Colors in the photographs may differ slightly from the color values cited in the detailed botanical description which accurately describe the colors of the new *Zamioculcas.*

FIG. 1. comprises a side perspective view of a typical plant of 'HANSOTI13'.

Figure 2:
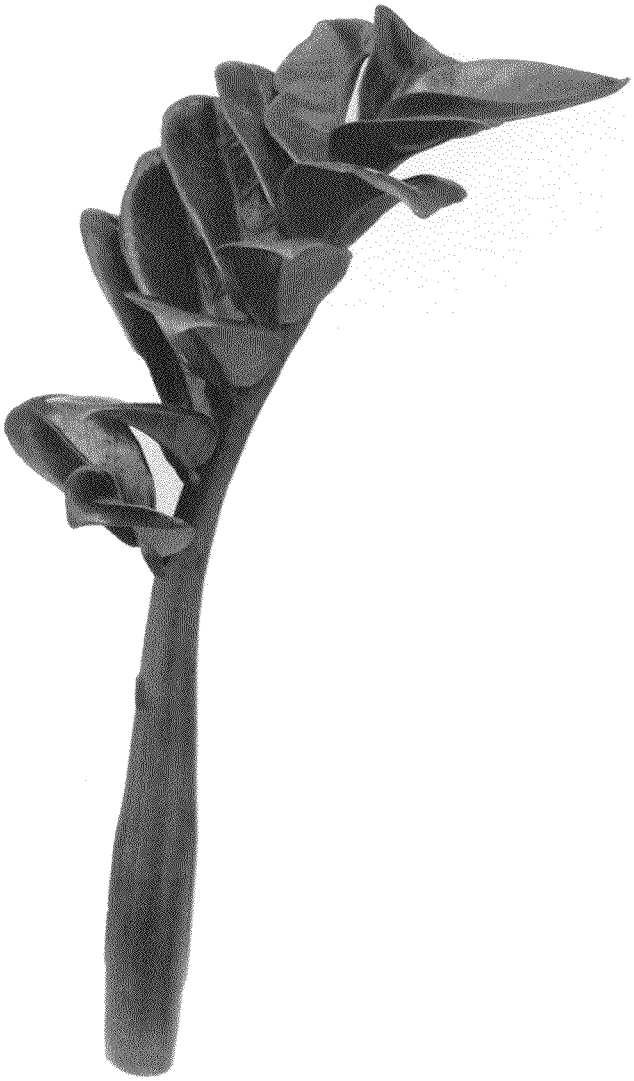

FIG. 2 is a close-up view of a typical whole leaf of 'HANSOTI13'.

Figure 3:
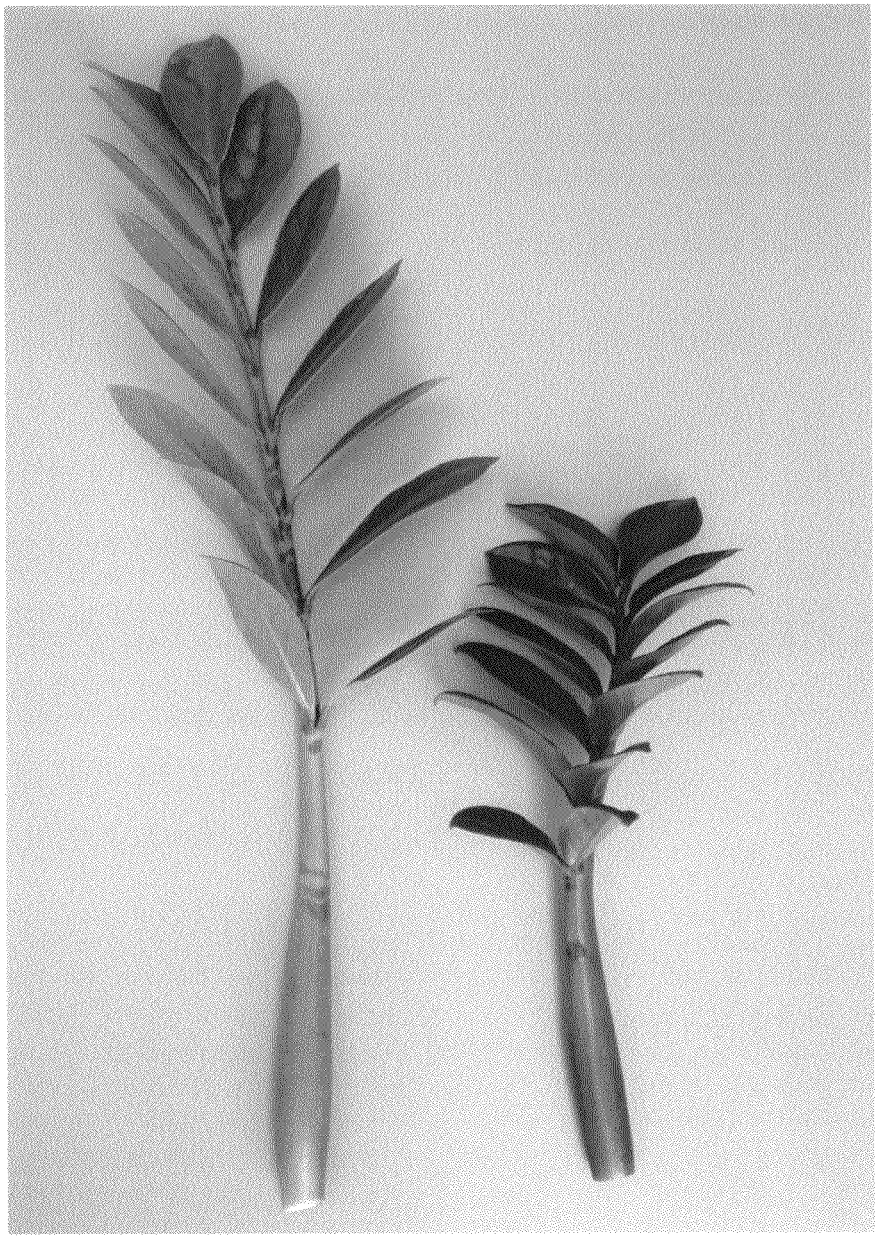

FIG. 3 illustrates a comparison of the leaf of 'HANSOTI13' with that of the, widely grown known variety *Zamioculcas zamiifolia*. Foliage of *Zamioculcas zamiifolia* is the larger leaf on the left of the figure. Foliage of the new variety is the small leaf on the right of the figure.

DETAILED BOTANICAL DESCRIPTION

The aforementioned photographs and following observations, measurements and values describe plants of the new *Zamioculcas* grown in Vangani, near Mumbai, India in a poly-covered, simple greenhouse during the summer and autumn and under conditions which closely approximate commercial production in tropical countries but warmer and drier than many western growing areas. During the production of the plants, day temperatures ranged from 25° C. to 38° C., night temperatures ranged from 15° C. to 25° C. and light levels under diffuse plastic and 50% shade net.

Plants had been growing in 13-cm containers for about 13 months when the photographs and the description were taken. In the detailed description, color references are made to The Royal Horticultural Society Colour Chart, 2001 Edition, except where general terms of ordinary dictionary significance are used. It should be noted that given time and potting into larger pots the cultivar 'HANSOTI13' will grow up to 50 cm tall and maybe taller. However, even at this size the core characteristics of short internodes, more leaves per leaf, stiff and strong petioles and overall urn shape of plant continue to hold true.

Botanical classification: *Zamioculcas zamiifolia* 'HANSOTI13'.

PROPAGATION

Typical: By vegetative leaf cuttings.

Time to initiate roots, summer: About 4 weeks at temperatures of 28° C. to 35° C.

Time to initiate roots, winter: About 6 weeks at temperatures of 15° C. to 25° C.

Time to produce a rooted young plant, spring/summer: About 20 weeks at temperatures of 22° C. to 30° C.

Time to produce a rooted young plant, autumn/winter/spring: About 30 weeks at temperatures of 20° C. to 25° C.

Root description: Free branching, dense. Fleshy when plants mature; white to light brown in color. Plants have large, shapeless light brown tuber from which roots & leaves arise.

PLANT

Plant habit: Upright and compact stiff leaves in rosettes; pinnately compound leaves developing in basal rosettes; typically about three basal rosettes develop per plant. Appropriate for 8.5-cm and larger containers.

Plant shape: Whole plant urn shaped.

Plant height: About 25 cm from top of pot to highest leaf.

Plant spread: About 25 cm in 13 cm pot.

Growth rate: Moderate.

Branching: Non-branching with leaves arising as a rosette or clump directly from tuber.

Number of clumps: Typically 2-3 per plant.

Number of leaves per clump: 3-6 leaves.

FOLIAGE

Leaf:

*Arrangement*.—Pinnately compound; about three to six leaves per basal rosette each with about 12-24 leaflets; leaflets have short petiolules of 4-5 mm.

Leaflet:

*Shape of blade*.—Obtuse.

*Aspect*.—Concave or reflexed.

*Base*.—Rounded.

*Apex*.—Acute.

*Margin*.—Entire.

*Average length*.—6 cm.

*Average width*.—3 cm.

*Texture of top surface*.—Glabrous, very glossy.

*Texture of bottom surface*.—Glabrous, matte.

*Color*.—Young foliage upper side: Near R.H.S. Yellow-Green 144A. Young foliage under side: Near R.H.S. Yellow-Green 144A. Mature foliage upper side: Near R.H.S. Yellow-Green-147A. Mature foliage under side: Near R.H.S. Yellow-Green 146A.

*Venation*.—Type: Pinnate. Color: Upperside: Near R.H.S. Yellow-Green-147A. Underside: Near R.H.S. Yellow-Green-147B.

Petiole:

*Length*.—Approximately 17 cm, continuing as rachis bearing the leaflets.

*Width*.—At narrowest point: Approximately 10 to 15 mm. At widest point: Approximately 20 to 25 mm.

*Color*.—Near RHS Yellow-Green 147A and 148A, irregularly blotched with Greyed-Green N189A.

*Strength*.—Very strong, stiff and succulent.

*Texture*.—Smooth, glabrous.

Rachis:

*Length*.—Approximately 15 cm.

*Diameter*.—Approximately 12 mm tapering to 5 mm.

*Color*.—Near R.H.S. Yellow-Green 148A.

*Other characteristics*.—Tapers to end in a pair of leaflets.

Petiolule:

*Length*.—Approximately 4 to 5 mm.

*Diameter*.—Approximately 3 mm.

*Color*.—Near R.H.S. Greyed-Green N189A.

*Other characteristics*.—Connects leaflets to rachis, continuing into the leaflet as the mid-rib.

OTHER CHARACTERISTICS

Flowering: Not observed to date.

Disease resistance: Neither resistance nor susceptibility to the normal diseases found in *Zamioculcas* has been observed.

Drought tolerance and cold tolerance: High drought resistance, can be kept dry for extended periods without appearance of damage.

Fruit/seed production: No fruits/seeds detected to date.

Other distinctive characteristics: Overall commercially interesting appearance. Dark green glossy leaves, very short internode spaces giving a lot of leaflets on each rachis and a genuine compact look. Looks like a plant of *Zamioculcas zamiifolia* treated with strong growth retardant, but is a naturally compact stable mutation.

What is claimed is:

1. A new and distinct cultivar of *Zamioculcas* plant named 'HANSOTI13' as herein illustrated and described.

* * * * *